United States Patent
Camps Díez et al.

(10) Patent No.: US 7,537,918 B2
(45) Date of Patent: May 26, 2009

(54) PROCESS OF PRODUCING POLYUNSATURATED FATTY ACIDS WITH YEASTS THROUGH THE INCORPORATION OF OLEFINIC OR ACETYLENIC SUBSTRATES

(75) Inventors: Francisco Camps Díez, Barcelona (ES); Sergio Rodríguez Ropero, Barcelona (ES); Gemma Fabriàs Domingo, Barcelona (ES); Benjamin Piña Capo, Barcelona (ES)

(73) Assignee: Consejo Superior De Investigaciones Cientificas, Madrid (ES)

( * ) Notice: Subject to any disclaimer, the term of this patent is extended or adjusted under 35 U.S.C. 154(b) by 165 days.

(21) Appl. No.: 11/096,240

(22) Filed: Mar. 31, 2005

(65) Prior Publication Data

US 2005/0227339 A1    Oct. 13, 2005

Related U.S. Application Data

(63) Continuation of application No. PCT/ES03/00498, filed on Oct. 1, 2003.

(30) Foreign Application Priority Data

Oct. 4, 2002    (ES) ............................... 200202282

(51) Int. Cl.
*C12P 7/62* (2006.01)
*C12P 7/64* (2006.01)
(52) U.S. Cl. ...................... 435/134; 435/135
(58) Field of Classification Search ............... 435/134, 435/135
See application file for complete search history.

(56) References Cited

U.S. PATENT DOCUMENTS

| | | | |
|---|---|---|---|
| 4,164,505 A | 8/1979 | Krajca | |
| 5,208,356 A | 5/1993 | Pariza et al. | |
| 6,060,304 A | 5/2000 | Pariza et al. | |
| 6,316,645 B1 | 11/2001 | Sih et al. | |
| 6,319,950 B1 | 11/2001 | Seidel | |

OTHER PUBLICATIONS

Abad, J.L. et al, 2001, Insect Biochemistry and Molecular Biology. 31:799-803.
Broadwater, J.A. et al, 2001, Journal of Inorganic Biochemistry, 78:7-14.
McDonough et al, 1992, Journal of Biological Chemistry, 267:5931-5936.
Gunstone, Lipid Synthesis and Manufacture, Sheffield Academic Press, 1999.
DeJarlas et al, J. Am. Oil Chem. Soc, 1971, 48, 21.
Frankel, Am. Oil Chem. Soc., 1970, 47, 33.
Bernas et al, Chem. Comun, 2002, 1142-3.
Warwel et al, Biotechnology Letters, 2000, 22(14), 1151-55.
Michinaka et al, J. Oleo Science 2001, 50(5): 359-365.

*Primary Examiner*—Herbert J. Lilling
(74) *Attorney, Agent, or Firm*—Klauber & Jackson, LLC

(57) ABSTRACT

The invention relates to a process of producing polyunsaturated fatty acids through the incorporation of olefinic or acetylenic fatty acids with a chain length of 13-18 carbon atoms as substrates with a haploid or diploid wild strain of *Saccharomyces cerevisiae* yeast W 303a or ΔElo1, which can be used to generate a novel linkage with configuration Z in position 9 of said substrates. The novel desaturation is only produced if the original unsaturation in the administered products has configuration E or is an acetylene. Moreover, if the original linkage has configuration Z, the substrate is recovered unaltered.

7 Claims, No Drawings

PROCESS OF PRODUCING POLYUNSATURATED FATTY ACIDS WITH YEASTS THROUGH THE INCORPORATION OF OLEFINIC OR ACETYLENIC SUBSTRATES

RELATED APPLICATIONS

The present application is a Continuation of co-pending PCT Application No. PCT/ES2003/000498, filed Oct. 1, 2003 which in turn, claims priority from Spanish Application Ser. No. P200202282, filed on Oct. 4, 2002. Applicants claim the benefits of 35 U.S.C. §120 as to the PCT application and priority under 35 U.S.C. §119 as to said Spanish application, and the entire disclosures of both applications are incorporated herein by reference in their entireties.

SECTOR OF THE ART

Production of polyunsaturated fatty acids for their use in the pharmaceutical, agroalimentary or cosmetic industries and as synthesis intermediaries in fine chemistry. Conjugate linoleic acids (CLA). Biotechnology sector.

STATE OF THE ART

In order to tackle the growing demand for polyunsaturated fatty acids in the pharmaceutical, agroalimentary or cosmetic industries, the extraction of natural sources has been turned to, where they are found in the form of complex mixtures from which it is practically impossible or very laborious to isolate the individual products by chromatographic methods or organic synthesis has to be applied as an alternative. Owing to the required stereospecificity, synthetic products are generally prepared in small quantities, their cost is very high and they are only used in research.

For that reason, natural sources have been turned to for preparing concentrates of polyunsaturated fatty acids by various methods such as molecular distillation of methyl esters, separation with urea, use of lipases for discrimination in the hydrolysis of triglycerides, exploiting the specificity with regard to the sterificated positions of the glycerol, to the nature of the ester, to the length of the chain and to the position of the double bonds (Lipid Synthesis and Manufacture, Ed. by Frank D. Gunstone, Sheffield Academic Press, 1999, England).

Likewise, methods can be found in the literature for the preparation of conjugated diene fatty acids starting from non-conjugated acids. Among them, conjugate linoleic acids (CLA) are the most important on account of their capacity to reduce or eliminate cancer (Seidel, MC 2001, U.S. Pat. No. 6,319,950), to prevent cardiovascular diseases, to improve the immune system and to help in the treatment of obesity.

These conjugate linoleic acids (CLA) are obtained as mixtures by isomerisation of linoleic acid, cis-9, cis-12-octadienoic acid, in homogeneous medium by means of using bases such as aqueous alkaline hydroxide in a tubular flow reactor at a pressure of 2300 psi and high temperatures (Krajca, K. E. 1979, U.S. Pat. No. 4,164505) or sodium methoxide (Iweta T. et al. 1998 EP0839897 A1) and deprotonation at temperatures between −78 and −20° C. with a super-strong organic base such as sec-butyllithium, Schlosser base or potassium trimethylsilylmethylure (Sih. Ch and Chen Ch-A, 2001 U.S. Pat. No. 6,316,645). Homogeneous catalysts have also been used such as tris(triphenylphosphine) chlororhodium (De Jarlas W., and Gast L., J., Am. Oil Chem. Soc, 1971, 48, 21) and arene chromocarbonyl complexes (Frakel, E., J. Am. Oil Chem. Soc., 1970, 47, 33) which facilitate matters so that the isomerisation reaction can be conducted at temperatures below the 180-200° C. required in the above case. Nevertheless, these catalysts are difficult to eliminate and are not compatible with the environment. For that reason, a process has recently been developed using an Ni catalyst supported on a zeolite preactivated with hydrogen which permits the isomersation to be carried out in a solution of n-decane or 1-octanol at temperatures of 80-120° C. (Bernas, A. et al., Chem. Comun, 2002, 1142-3).

Nevertheless, it has been confirmed that the component responsible for the anti-carcinogenic effects of CLA is the cis-9, trans-11 isomer, due to which it would be necessary to develop specific isomerisation methods for obtaining that isomer. This has been attempted by reaction of lineoleic acid with a linoleate isomerase of the bacterium of the rumen *Butyrivibrio fibrisolvens* (Pariza, M. W. and Ha Y. L. 1993. U.S. Pat. No. 5,208,356) and by combination of a substantially pure preparation of a strain of *Lactobacillus* which is capable of converting fatty acids with non-conjugated double bonds in the configuration cis-9, cis-12 into fatty acids with conjugated double bonds among which at least 50% contain double bonds with the configuration cis-9, trans11 (Pariza M W and Yang X-Y, 2000 U.S. Pat. No. 6,060,304). Moreover, a study has been conducted on the selectivity of lipases in the sterification of the mixture of CLA with n-butanol in n-hexane in which a preference of the lipases of *Candida cylindricea* and *Mucor miehei* was observed in the sterification of the desired isomer cis-9, trans-11 (Warwel, S.; Borgdorf, R.; Biotechnology Letters, 2000, 22(14), 1151-55).

As described below in the process of the present invention, this active isomer can be obtained unequivocally by specific desaturation of trans 11-octadecenoic acid.

For the production of polyunsaturated fatty acids, the yeast *Saccharomyces cerevisiae* has been used, genetically transformed with the incorporation of genes of various desaturates of fatty acids of different origin (Suzuki, O, et al., W. O. 2001075069 A1, Michinika, Y., et al., J. of Oleo Science 2001, 50(5): 359-365).

In the present invention a Δ-9 desaturase of *Saccharomyces cerevisiae* is used for the selective production of polyunsaturated fatty acids.

DESCRIPTION OF THE INVENTION

Brief Description

The present invention relates to a process of producing polyunsaturated fatty acids through the incorporation of olefinic or acetylenic fatty acids with a chain length of 13-18 carbon atoms as substrates with a haploid or diploid wild strain of *Saccharomyces cerevisiae* yeast W 303a or ΔElo1, which can be used to generate a novel linkage with configuration Z in position 9 of said substrates. The novel desaturation is only produced if the original unsaturation in the administered products has configuration E or is an acetylene, while if the original linkage has configuration Z, the substrate is recovered unaltered.

DETAILED DESCRIPTION OF THE INVENTION

The present invention is based on the fact that the inventors have observed that the addition of mono-unsaturated fatty acids containing one or several unsaturations starting from position C-11 of the chain as a substrate to strains of the species *Saccharomyces cerevisiae* permits the production of polyunsaturated fatty acids of chain length C13-C18 as an additional unsaturation of configuration Z in position 9 of the original chain by Δ-9 desaturase of the yeast.

More specifically, the present invention refers to the production of polyunsaturated fatty acids of chain length C13-C18 employing a process consisting of cultures of haploid or diploid W303a *Saccharomyces cerevisiae* strains (American Type Culture Collection) and ΔElo1 (elongase deficient) genetically modified (EUROSCARF) to which fatty acids containing one or several unsaturations starting from position C-11 of the chain, have been incorporated as substrates in order to produce compounds with an additional unsaturation of configuration Z in position 9 of the chain, among others, belonging to the following group: Z9,E11:13; Z9,E11:14; Z9,E11:15; Z9,E11:16; Z9,E11:18; Z11:13; Z11:14; Z11:15; Z11:16 and Z9,11,11:13 by means of incubation with the haploid or diploid W303a strains, and Z9,E11:13; Z9,E11:14Z9,E11:15; Z9,E11:16; Z9,E11:18; Z11:13; Z11:14; Z11:15; Z11:16 and Z9,11,11:13 by means of incubation with the ΔElo1 strains, respectively.

It has been observed that the substrates supplied to the yeast with double bonds with configuration E or trans are desaturated by Δ-9 desaturase of the yeast much faster than the corresponding Z or cis isomers with the formation of a new double bond of configuration Z or cis in position 9 of the aliphatic chain producing the corresponding derivatives Z9E11 (cis9, trans11). Likewise, as indicated below in Table 1, it has been found that in cases of using haploid or diploid W303a strains, a partial lengthening is produced of two of the chain of the original substrate, with desaturation being maintained in position 9 of the new substrate, an elongation that is not produced when ΔElo1 strains are used.

The products obtained can have application in the pharmaceutical industry as anti-carcinogens (for example, the compound Z9E11), in the agroalimentary industries as nutriceuticals, in cosmetics and in the fine chemical industry as intermediaries for the synthesis of insect pheromones for application in integrated control of plagues of insects by bio-rational methods.

Without implying a limitation on the application of the present invention which is defined in the claims specified further below, we are going to describe a specific example of application.

EXAMPLES OF EMBODIMENT

Example 1

Process of Producing Polyunsaturated Fatty Acids with Yeasts through the Incorporation of Olefinic or Acetylenic Substrates Yeast Cultures with Substrates The growth of colonies of haploid or diploid W303a and ΔElo1 (elongase deficient) yeast was carried out in solid medium with plates of YPD-agar at 37° C. for 24 h. Starting from a 1M ethanolic solution of substrate fatty acid, it is added to a single colony of yeast in 2 mL of liquid medium YPD-tergitol (1%) in such a way that the fatty acids are in a final concentration of 0.25-1 mM of substrate, preferably 0.5 mM. The mixture is left to grow for 24-48 hours, preferably 24 hours at 37° C. with stirring at 200-300 rpm, preferably 200 rpm.

Process for Extraction of the Different Acids

The culture medium is transferred to an Eppendorf type flask of 1.5 ml and is centrifuged at 3000 rpm for 5 minutes. The supernatant is discarded and the remaining culture medium is transferred and centrifuged under the same conditions as previously. The supernatant is discarded, it is washed with 1 mL of water, and the operations of washing, centrifugation and elimination of supernatant are repeated twice more. Finally, it is centrifuged at 3000 rpm for 2 min. in order to totally eliminate the water. 1 mL of $CHCl_3$:MeOH (2:1) is added and it is left stirring with a mechanical arm for 1 h. Finally, it is centrifuged at 13200 rpm for 15 s., the organic extract is passed to a 3 mL flask and the solvent is evaporated.

The residue of fatty acids was methanolised by the addition of 0.5 mL of a 0.5N solution of KOH in MeOH, followed by neutralisation after 30 min with 0.5 ml of 1N HCl and extraction with 0.5 mL of hexane. The organic layer is separated, it is concentrated to a volume of 20 μL and analysed by CG-EM.

Analysis of the Acids Obtained

The methyl esters are analysed by CG-EM in an HP-1 apolar column with the following temperature programme 80° C. (0)/5/200(0)10/300 (10).

The position of the conjugated double bonds was analysed by CG-EM by the formation of complexes with MTAD (4-methyl-1,2,4-triazolin-3,5-dione). These complexes are formed by the addition of 2.5 μL of a solution of 1.2 mg of MTAD in 1 mL of $CH_2Cl_2$ on 10 μL of hexane extract, stirring and evaporating as far as a final volume of 2 μL. It is injected in CG-EM with the following temperature programme 80° (0)/5/200(0)10/300 (25).

The position of non-conjugated double bonds was determined by the formation of complexes with DMDS (dimethyl disulphide). These complexes are formed by addition on 20 •L of hexane extract, 50 μL of dimethyl disulphide and a drop of iodine solution in diethyl ether (60 mg/mL). The mixture is warmed at 45-50° for 72 h.

Once that time has passed, it is diluted with hexane, the iodine is eliminated with a saturated solution of $Na_2S_2O_3$, it is washed with $H_2O$ and the organic phase is separated. The volume of hexane is concentrated to 20 μL and is analysed by CG-EM injecting 1 μL under the conditions stated above.

Results

The substrates used were a series of mono-unsaturated fatty acids of 13-18 carbon atoms in the chain which in position 11 possessed a double bond of Z or E stereochemistry or a triple bond.

These acids were commercially accessible or were synthesised in our laboratory by conventional methods. As indicated in Table 1, the substrates with E or trans stereochemistry in the double bond or a triple bond are desaturated by the yeast in position 9 giving the corresponding derivatives Z9E11, while under the incubation conditions, 24 hours at 37° stirring at 200 rpm, the corresponding substrates with Z or cis stereochemistry are recovered unaltered.

Haploid and diploid W303a strains containing elongase are capable of lengthening the chain in 2, depending on the substrate. In these cases the new fatty acids formed with unsaturations in positions 13 or 15 can be desaturated to the corresponding Z9E13 and Z9E15. In the case of substrates with double bonds of configuration Z11, no later desaturation is observed in spite of the corresponding substrates with double bonds of configuration Z13 and Z15 being obtained by elongation of the chain. Moreover, the Z9E11 dienes that are formed can be lengthened to the corresponding Z11E13 and Z13E15.

When strains of elongase deficient yeast (ΔElo1) are used only the dienes Z9E11 resulting from the desaturation are obtained.

In all cases, endogenous acids belonging to the yeast are observed, such as palmitoleic (Z9:16) and oleic (Z9:18).

TABLE 1

| Substrate acid* | Yeast strain | Products detected Majority | Products detected Minority |
|---|---|---|---|
| E11:13 | Haploid or diploid W303a | Z9,E11:13 | Z11,E13:15 Z9E13:15 E13:15 |
| E11:13 | ΔElo1 | Z9,E11:13 | — |
| E11:14 | Haploid or diploid W303a | Z9,E11:14 | Z11,E13:16 E13:16 |
| E11:14 | ΔElo1 | Z9,E11:14 | — |
| E11:15 | Haploid or diploid W303a | Z9,E11:15 | Z11,E13:17 E13:17 Z9E13:17 |
| E11:15 | ΔElo1 | Z9,E11:15 | — |
| E11:16 | Haploid or diploid W303a | Z9,E11:16 | Z11,E13:18 Z9E13:18 E13:18 |
| E11:16 | ΔElo1 | Z9,E11:16 | — |
| E11:18 | Haploid or diploid W303a | Z9,E11:18 | — |
| E11:18 | ΔElo1 | Z9,E11:18 | — |
| Z11:13 | Haploid or diploid W303a | Z11:13 | Z13:15 |
| Z11:13 | ΔElo1 | Z11:13 | — |
| Z11:14 | Haploid or diploid W303a | Z11:14 | Z13:16 |
| Z11:14 | ΔElo1 | Z11:14 | — |
| Z11:15 | Haploid or diploid W303a | Z11:15 | Z13:17 |
| Z11:15 | ΔElo1 | Z11:15 | — |
| Z11:16 | Haploid or diploid W303a | Z11:16 | Z13:18 |
| Z11:16 | ΔElo1 | Z11:16 | — |
| 11,11:13 | Haploid or diploid W303a | Z9,11,11:13 | Z111313:15 13,13:15 |
| 11,11:13 | ΔElo1 | Z9,11,11:13 | — |

*Configuration and unsaturation position: chain length

The invention claimed is:

1. A process for production of polyunsaturated fatty acids comprising the following steps:
    a) incubating monounsaturated acetylenic fatty acids or monounsaturated olefinic fatty acids with a double bond of E type with strains of *Saccharomyces cerevisiae* yeast in liquid medium; and
    b) extracting and purifying the polyunsaturated fatty acids of the culture medium, product of the incubation of a).

2. A process according to claim 1 wherein the strain of *Saceharomyces cerevisiae yeast* is selected from the group consisting of W303a haploid strain containing elongase, W303a diploid strain containing elongase and elongase deficient ΔElo1 strain.

3. A process according to claim 1 wherein said acetylenic fatty acids or olefinic fatty acids comprise a mono-unsaturated fatty acid of 13 to 18 carbon atoms in the chain which in position 11 possesses a double bond of configuration Z or E or a triple bond.

4. A process according to claim 1 wherein said product resulting from said incubation, that comprises a double bond in position 9, can be lenghtened in its chain by elongases from the haploid or diploid W303 a yeast, giving new products containing double bonds in positions 11 and 13.

5. A process according to claim 4 wherein said polyunsaturated product resulting from said process is selected from the group consisting of Z9,E11:13; Z9,E11:14; Z9,E11:15; Z9,E11:16; Z9,E11:18; Z11:13; Z11:14; Z11:15; Z11:16 and Z9,11,11:13.

6. A process according to claim 1 wherein the resulting product from the incubation with a double bond in position 9 is not lengthened in its chain and the strain used is the elongase deficient δElo1 strain.

7. A process according to claim 6 wherein the the polyunsaturated product resulting from said process is selected from the group consisting of Z9,E11:13; Z9,E11:14; Z9,E11:15; Z9,E11:16; Z9,E11:18; Z11:13; Z11:14; Z11:15; Z11:16 and Z9,11,11:13.

* * * * *